| United States Patent [19] | [11] Patent Number: 4,514,503 |
| Orelup | [45] Date of Patent: Apr. 30, 1985 |

[54] REAGENT AND PROCESS FOR DETECTING FURFURAL IN PETROLEUM PRODUCTS

[75] Inventor: Richard B. Orelup, Upper Saddle River, N.J.

[73] Assignee: Morton Norwich Products, Chicago, Ill.

[21] Appl. No.: 413,833

[22] Filed: Sep. 1, 1982

[51] Int. Cl.³ .................... G01N 21/78; G01N 33/26
[52] U.S. Cl. ........................................ 436/60; 436/56; 436/93
[58] Field of Search ................ 436/56, 93, 60; 422/61

[56] References Cited

U.S. PATENT DOCUMENTS

| 2,109,645 | 3/1938 | Lankelma | 436/56 |
| 3,764,273 | 10/1973 | Turner et al. | 435/56 |
| 3,986,834 | 10/1976 | Steinbrink, Jr. | 422/61 X |
| 4,049,393 | 9/1977 | Orelup | 436/56 X |
| 4,209,302 | 6/1980 | Orelup | 44/59 |

OTHER PUBLICATIONS

Habenstein, Chemical Abstracts, vol. 91, 1979, No. 91:76759d.

Primary Examiner—Arnold Turk
Attorney, Agent, or Firm—George F. Wheeler; Jack Axelrood

[57] ABSTRACT

A two-component liquid reagent and process is provided for detecting the presence of furfural in petroleum products. The reagent comprises the following two components which are stored separately from each other and are combined prior to admixture with the petroleum product:

First component
  from about 15 to about 22 percent of a primary amine selected from the group consisting of aniline, meta aminophenol, para anisidine, meta toluidine and para toluidine;
  from about 35 to 45 percent of diethylene glycol;
  from about 35 to about 45 percent of ethanol; and
  from about 1 to 2 percent of an antioxidant;

Second Component
  from about 18 to about 25 percent of an acid selected from the group consisting of citric acid, lactic acid, formic acid and phosphoric acid;
  from about 35 to about 45 percent of diethylene glycol; and
  from about 35 to 45 percent of ethanol, with the proviso that when in the first component the amine is aniline then in the second component the acid is selected from the group consisting of citric acid, lactic acid and formic acid.

The process comprises combining the two separate components of the liquid reagent with each other prior to use, admixing the combined components with a petroleum product containing furfural, shaking the resultant mixture, allowing the mixture to separate and observing a red color characteristic of furfural in the lower layer.

Alternately, the process may be carried out by combining the second component of the two-component liquid reagent with the petroleum product, followed by admixture with the first component to obtain two separate layers in which the red color characteristic of furfural is observed in the lower layer.

25 Claims, No Drawings

REAGENT AND PROCESS FOR DETECTING FURFURAL IN PETROLEUM PRODUCTS

BACKGROUND OF THE INVENTION

1. Field of the Invention

The laws of certain Provinces of Canada and of many European countries provide for taxes to be imposed on motive fuels, such as diesel oil, but a lesser tax or none at all on heating oil. In view of the fact that diesel oil and heating oil are very similar in their chemical and physical properties, it becomes necessary to mark, tag or otherwise identify the untaxed oils, or gasolines, from those that are taxed.

2. Description of the Prior Art

Furfural has been used widely as a marker for petroleum products for the purpose of tagging or identifying same. In fact, the laws of certain Provinces of Canada specifically require that furfural be used for this purpose.

The property of furfural to form colored compounds with primary aromatic amines in an acidic medium has been known for more than 100 years. One important application of the furfural color reaction is its use as a marker for petroleum fuels. A marker, or identifying agent is used to detect a fuel which may be subjected to differing tax rates, depending on its application, such as motor vehicle diesel engine fuel or light heating oil. Another application may be detection of blending lower priced or lower grade fuels into higher grade products. Examples are kerosene or low octane gasoline into higher octane gasoline.

The only well recognized reagent system for furfural detection in petroleum products is a solution of aniline in acetic acid (generally about 10% aniline). The reagent commonly is used by governmental agents in field test procedures by mixing about one volume part of reagent with 10 volume parts fuel sample in a clear container and shaking vigorously for a short time. Upon standing, the reagent layer settles to the bottom. For fuel samples containing furfural, the reagent layer is colored bluish red, with an intensity depending on furfural content. If no furfural is present, the reagent layer remains colorless.

With some elaborations, the field test procedure also can be modified to form the basis for quantitative laboratory furfural determination.

However, the preceding test description represents ideal conditions, frequently not encountered in reality. Furfural typically is employed at about 10 parts per million as a petroleum marker. Under very favorable circumstances, it is detectible at concentrations down to 0.5 parts per million, or approximately 5% marked fuel in a mixture with 95% unmarked fuel. Under common unfavorable conditions, the minimum test sensitivity may be only 2.0 parts per million, a situation preventing detection below 20% marked fuel. Since the area of 5%-20% marked fuel blending normally is of high interest to enforcement authorities improved test reagents are needed.

However, there are certain drawbacks with the conventional aniline/acetic acid reagent system, such as:

1. The aniline/acetic acid combination extracts appreciable impurities from fuel samples. These comprise both naturally colored materials and fuel components other than furfural that become colored on contact with the acidic reagent. They produce yellow to brown colors in the reagent, whose intensity obscures or masks a furfural color reaction, and in some situations may even produce a false positive test.

The characteristics of light heating oils and gasolines in this respect vary widely so there is no way to predict the degree of interfering coloration resulting from any particular fuel sample. Additionally, the characteristics of a given fuel change wth age, particularly in products containing severely cracked fractions.

2. A varying proportion of reagent is dissolved by the fuel sample. This ranges upward to almost 100% in some gasolines, effectively destroying the test by simply being difficult to see or by further concentrating fuel color impurities in the extract layer.

3. Stability of the furfural reaction color varies widely, and is generally relatively shortest in the darkest, least stable fuels. Here, the true red furfural color commonly is altered to orange or orange-brown because of the superimposed natural color. The natural color increases rapidly on standing while the positive test shade becomes browner. As a result, weaker positive tests often are visible only for a few seconds, in unfavorable situations.

4. Stability of the reagent itself. When aniline and acetic acid are mixed, the combination immediately begins to develop a yellow color. It increases more or less rapidly, particularly during the first 24-48 hours, and depending upon exposure to light, air and ambient temperature. As the color deepens to orange, loss of reagent efficiency takes place.

Even though the reagent retains some activity for periods of a week to a month, the simultaneous development of interfering background color severely decreases test sensitivity. This problem limits use of prepacked test kits and reagent supplies that are desirable in practical applications.

5. Aniline/acetic acid freezes at +16° C., making it difficult or impossible to use in cold climates. The most important period wherein furnace oil is substituted in part or all for diesel fuel is during the winter months. Temperatures under field test conditions in areas where furfural is of interest, range to −30° C., and are rarely above 0° C. during the critical period.

6. The aniline/acetic acid reagent is corrosive to the skin and possesses an offensive irritating odor. Both properties create resistance to use by law enforcement personnel.

Accordingly, it would be desirable and is an object of this invention to provide a reagent for the detection of furfural in petroleum products, which reagent overcomes the aforenoted disadvantages of an aniline/acetic acid reagent, and has the following advantageous characteristics:

1. Extracts only a minimal amount of impurities from the petroleum product.
2. Is essentially insoluble in petroleum products so that at least about 80 percent of the reagent volume used separates from the petroleum product with which it is mixed to form a separate recognizable layer.
3. The duration and stability of the positive test color is increased under all test conditions.
4. The test sensitivity is increased so that detection of furfural may be made at concentrations as low as about 0.25 part per million.
5. The stability of the two-component liquid reagent is increased.

6. The freezing point of each component of the two-component liquid reagent is below −40° C., thus making possible cold weather testing.
7. Each component of the two-component liquid reagent is less corrosive to the skin than the aniline/acetic acid reagent.

The fulfillment of these desiderata and object of this invention may be more readily appreciated by reference to the following specification, examples and appended claims.

SUMMARY OF THE INVENTION

The present invention provides a novel two-component liquid reagent comprising a first component and a second component for detecting the presence of furfural in petroleum products, each component of said liquid reagent being stored separately from the other component and both components being combined with each other prior to admixture with a petroleum product, said components comprising the following compositions on a weight basis:

First Component
   from about 15 to about 22 percent of a primary amine selected from the group consisting of aniline, metal amino phenol, para anisidine, metal toluidine and para toluidine;
   from about 35 to about 45 percent of diethylene glycol;
   from about 35 to about 45 percent of ethanol; and
   from about 1 to 2 percent of an antioxidant; and
Second Component
   from about 18 to about 25 percent of an acid selected from the group consisting of citric acid, lactic acid, formic acid and phosphoric acid;
   from about 35 to about 45 percent of diethylene glycol; and
   from about 35 to 45 percent of ethanol, with the proviso that when in the first component the amine is aniline then in the second component the acid is selected from the group consisting of citric acid, lactic acid and formic acid.

The present invention also provides a process for detecting the presence of furfural in a petroleum product containing same, said process comprising admixing in a suitable container with a major quantity of said petroleum product a minor quantity of a first component of a two-component liquid reagent, said first component comprising on a weight basis from about 18 to about 25 percent of an acid selected from the group consisting of citric acid, lactic acid, formic acid and phosphoric acid, from about 35 to about 45 percent of diethylene glycol and from about about 35 to about 45 percent of ethanol, adding to said admixture of petroleum product and said first component a minor quantity of the second component of said liquid reagent, said second component comprising on a weight basis from about 15 to about 22 percent of a primary amine selected from the group consisting of aniline, meta aminophenol, para aminophenol, meta toluidine and para toluidine, from about 35 to about 45 percent of diethylene glycol, from about 35 to about 45 percent of ethanol and from about 1 to about 2 percent of an antioxidant, with the proviso that when in the first component the amine is aniline then in the second component the acid is selected from the group consisting of citric acid, lactic acid and formic acid, shaking the resultant mixture and allowing the mixture to stand and separate into two layers whereupon a red color characteristic of furfural is visible in the lower layer.

In practice, the first and second components are combined with each other in a suitable container prior to admixture with a petroleum product containing furfural to produce the characteristic red color of the primary amine-furfural reaction in the separated lower layer. Alternately, the acid-containing component of the liquid reagent mixture may be combined with the furfural-containing petroleum product in a suitable container and then admixed with the amine-containing component to obtain a separated lower layer displaying the characteristic red color of the furfural primary amine reaction.

A minor quantity of equal amounts of the two components of the liquid reagent is added to a major quantity of petroleum product in carrying the test for the presence of furfural. The terms "minor" and "major" in this context mean that about 1 part (minor amount) of liquid reagent is used in admixture with from about 5 to about 15 parts (major amount) of petroleum product.

The preferred quantity of liquid reagent to be admixed with the petroleum product is about 10 parts of the combined components (5 parts of each component) to about 90 to 100 parts of petroleum product. However, it is understood that these proportions may be varied as indicated.

The preferred antioxidant is 2,6-di-t-butyl-4-methyl phenol, although it is understood that any suitable antioxidant is operable.

The term "petroleum product" as used herein refers to such petroleum-derived products as gasoline, diesel oils, motive oils, heating oils, lubricating oils, jet fuels, kerosenes and naphthas.

One preferred coomposition of the liquid reagent of this invention is when the amine of the primary amine-containing component is aniline and the acid of the acid-containing component is citric acid.

Another preferred composition is when the amine of the amine-containing component is meta aminophenol and the acid of the acid-containing component is phosphoric acid.

For a more complete understanding of the present invention, reference is now made to the following specific examples illustrating the present novel two-component liquid reagent for detecting furfural in petroleum products.

DESCRIPTION OF THE PREFERRED EMBODIMENTS

EXAMPLE 1

A two-component liquid reagent for detecting the presence of furfural was prepared by making the following solutions of first and second components which were stored separately:

|  | % By Weight |
|---|---|
| First Component |  |
| Aniline | 19 |
| Diethylene Glycol | 40 |
| Ethanol | 40 |
| 2,6-di-t-butyl-4-methyl phenol | 1 |
|  | 100% |
| Second Component |  |
| Citric Acid | 20 |
| Diethylene Glycol | 40 |
| Ethanol | 40 |

| | % By Weight |
|---|---|
| | 100% |

Five milliliters of the second component were placed in a 4 ounce test bottle. Immediately prior to use as a liquid reagent for detecting furfural, 5 ml. of the first component were admixed with the second component. Then 100 ml. of a petroleum product consisting of a mixture of 95 ml. of No. 2 Diesel Fuel and 5 ml. of No. 2 Furnace Oil (containing 10 ppm of furfural) were added to the first and second components mixture. The petroleum product contained 0.5 ppm of furfural.

After shaking the reagent and petroleum product mixture for 15 seconds, the mixture was allowed to stand for about 1 minute, whereupon approximately 8 ml. of the liquid reagent settled to the bottom of the test bottle to form a lower layer in which a bright red color was visible, indicating the presence of furfural.

EXAMPLE 2

The procedure of Example 1 was repeated except that the petroleum product was 100% of No. 2 Diesel Fuel containing no furfural. The separated lower layer of reagent was a pale yellow color which darkened very slowly but remained in sharp contrast to the red color of Example 1 for at least 10 minutes.

EXAMPLE 3

A two-component liquid reagent for detecting the presence of furfural was prepared by making the following solutions of first and second components which were stored separately:

| | % By Weight |
|---|---|
| First Component | |
| Meta aminophenol | 18 |
| Diethylene Glycol | 40 |
| Ethanol | 40 |
| 2,6-di-t-butyl-4-methyl phenol | 2 |
| | 100% |
| Second Component | |
| Phosohoric acid | 23 |
| Diethylene Glycol | 38.5 |
| Ethanol | 38.5 |
| | 100% |

A 4 ounce capacity test bottle was prepacked with 5 ml. of the second component. Ninety ml. of a petroleum product consisting of 90% Super Unleaded Gasoline (91 octane) and 10% of Kerosene (containing 10 ppm of furfural) was added to the test bottle. The petroleum product contained 1 ppm of furfural. Five ml. of the first component were then added to the petroleum product-second component mixture and the whole mixture was shaken for 15 seconds. After standing for 1 minute, about 7.5 ml. of the reagent settled to the bottom to form a lower layer having a strong bluish red color. This bluish red color increased in intensity for several minutes and remained very strong in color for 30 minutes.

EXAMPLE 4

The procedure of Example 3 was repeated except that the petroleum product was 100% unmarked Super Unleaded Gasoline (91 octane). The separated lower layer of reagent was a permanent pale yellow color.

EXAMPLE 5

The procedure of Example 3 was repeated except that 50 ml. of petroleum product was used with 5 ml. of a liquid reagent which was a 9:1 glacial acetic acid:aniline mixture. After shaking the reagent with the petroleum product and allowing to stand, there was no reagent separation.

EXAMPLE 6

The procedure of Example 1 was repeated except that the reagent used was a 9:1 glacial acetic acid:aniline mixture. After shaking this reagent with the petroleum product and allowing to stand, approximately 2 ml. of an orange-brown layer separated over a period of about 2-3 minutes, which became dark brown in color upon standing for an additional minute.

The results of Examples 1-6 demonstrate that the present reagent is a more effective means to detect the presence of furfural in petroleum products than is the currently used aniline/acetic acid reagent.

What is claimed is:

1. A two-component liquid reagent comprising a first component and a second component for detecting the presence of furfural in petroleum products, each component of said liquid reagent being stored separately from the other component and both components being combined with each other prior to admixture with a petroleum product, said components comprising the following compositions on a weight basis:

First Component
 from about 15 to about 22 percent of a primary amine selected from the group consisting of aniline, meta aminophenol, para anisidine, meta toluidine and para toluidine;
 from about 35 to 45 percent of diethylene glycol;
 from about 35 to about 45 percent of ethanol; and
 from about 1 to 2 percent of an antioxidant;

Second Component
 from about 18 to about 25 percent of an acid selected from the group consisting of citric acid, lactic acid, formic acid and phosphoric acid;
 from about 35 to about 45 percent of diethylene glycol; and
 from about 35 to 45 percent of ethanol, with the proviso that when in the first component the amine is aniline then in the second component the acid is selected from the group consisting of citric acid, lactic acid and formic acid.

2. The reagent of claim 1 wherein in the first component the primary amine is aniline and in the second component the acid is citric acid.

3. The reagent of claim 1 wherein in the first component the primary amine is meta aminophenol and in the second component the acid is phosphoric acid.

4. The reagent of claim 1 wherein in the first component the primary amine is aniline and in the second component the acid is lactic acid.

5. The reagent of claim 1 wherein in the first component the primary amine is aniline and in the second component the acid is formic acid.

6. The reagent of claim 1 wherein in the first component the primary amine is meta aminophenol and in the second component the acid is lactic acid.

7. The reagent of claim 1 wherein in the first component the primary amine is meta aminophenol and in the second component the acid is formic acid.

8. The reagent of claim 1 wherein in the first component the antioxidant is 2,6-di-t-butyl-4-methyl phenol.

9. The reagent of claim 1 wherein said acid is selected from the group consisting of citric acid, lactic acid and formic acid.

10. The reagent of claim 1 wherein said primary amine is selected from the group consisting of meta aminophenol, para anisidine, meta toluidine and para toluidine.

11. A process for detecting the presence of furfural in a petroleum product containing same, said process comprising admixing in a suitable containier with a major quantity of said petroleum product a minor quantity of a first component of a two-component liquid reagent, said first component comprising on a weight basis from about 18 to about 25 percent of an acid selected from the group consisting of citric acid, lactic acid, formic acid and phosphoric acid, from about 35 to about 45 percent of diethylene glycol and from about 35 to about 45 percent of ethanol, adding to said admixture of petroleum product and said first component a minor quantity of the second component of said liquid reagent, said second component comprising on a weight basis from about 15 to about 22 percent of a primary amine selected from the group consisting of aniline, meta aminophenol, para anisidine, meta toluidine and para toluidine, from about 35 to about 45 percent of diethylene glycol, from about 35 to about 45 percent ethanol and from about 1 to about 2 percent of an antioxidant, with the proviso that when in the first component the amine is aniline then in the second component the acid is selected from the group consisting of citric acid, lactic acid and formic acid, shaking the resultant mixture and allowing the mixture to stand and separate into two layers whereupon a red color characteristic of furfural is visible in the lower layer.

12. The process of claim 11 wherein the quantity of petroleum product ranges from about 5 to about 15 volumes per volume of the first and second components combined.

13. The process of claim 11 wherein in the first component the acid is citric and in the second component the primary amine is aniline.

14. The process of claim 11 wherein in the first component the acid is phosphoric acid and in the second component the primary amine is meta aminophenol.

15. The process of claim 11 wherein in the first component the acid is lactic acid and in the second component the primary amine is aniline.

16. The process of claim 11 wherein in the first component the acid is formic acid and in the second component the primary amine is aniline.

17. The process of claim 11 wherein in the first component the acid is lactic acid and in the second component the primary amine is meta aminophenol.

18. The process of claim 11 wherein in the first component the acid is formic acid and in the second component the primary amine is meta aminophenol.

19. A process for detecting the presence of furfural in a petroleum product containing same, said process comprising admixing in a suitable container a minor quantity of a first component of a two-component liquid reagent with a minor quantity of the second component of said liquid reagent, said first component comprising on a weight basis from about 18 to about 25 percent of an acid selected from the group consisting of citric acid, lactic acid, formic acid and phosphoric acid, from about 35 to 45 percent of diethylene glycol and from about 35 to about 45 percent of ethanol, said second component comprising on a weight basis from about 15 to about 22 percent of a primary amine selected from the group consisting of aniline, meta aminophenol, para anisidine, meta toluidine and para toluidine, from about 35 to about 45 percent of diethylene glycol, from about 35 to 45 percent of ethanol and from about 1 to about 2 percent of an antioxidant, with the proviso that when in the second component the amine is aniline then in the first component the acid is selected from the group consisting of citric acid, lactic acid and formic acid, adding to the admixture of said first and second components a major quantity of said petroleum product, shaking the resultant mixture of first and second components and petroleum product and allowing the mixture to separate into two layers whereupon a red color characteristic of furfural is visible in the lower layer.

20. The process of claim 19 wherein in the first component the acid is citric acid and in the second component the primary amine is aniline.

21. The process of claim 19 wherein in the first component the acid is phosphoric acid and in the second component the primary amine is meta aminophenol.

22. The process of claim 19 wherein in the first component the acid is lactic acid and the primary amine is aniline.

23. The process of claim 19 wherein in the first component the acid is formic acid and in the second component the primary amine is aniline.

24. The process of claim 19 wherein in the first component the acid is lactic acid and in the second component the primary amine is meta aminophenol.

25. The process of claim 19 wherein in the first component the acid is formic acid and in the second component the primary amine is meta aminophenol.

* * * * *